United States Patent [19]

Stapleton

[11] Patent Number: 4,746,805
[45] Date of Patent: May 24, 1988

[54] COMBINED DISTINCTNESS OF IMAGE AND GLOSS METER

[75] Inventor: Thomas T. Stapleton, Bloomfield Hills, Mich.

[73] Assignee: General Motors Corporation, Detroit, Mich.

[21] Appl. No.: 931,852

[22] Filed: Nov. 18, 1986

[51] Int. Cl.⁴ ............................................. G01N 21/55
[52] U.S. Cl. ..................... 250/571; 356/446; 356/447; 350/275
[58] Field of Search ............... 250/571, 559, 562, 274, 250/273, 275; 356/446, 447, 125, 445, 448

[56] References Cited

U.S. PATENT DOCUMENTS

| | | | |
|---|---|---|---|
| 2,315,282 | 3/1943 | Snow | 356/446 |
| 2,720,812 | 10/1955 | Middleton | 356/446 |
| 3,549,264 | 12/1970 | Christie | 356/446 |
| 3,850,526 | 11/1974 | Corey, III | 250/571 |
| 3,922,093 | 11/1975 | Dandliker et al. | 250/571 |
| 4,285,597 | 8/1981 | Lamprecht et al. | 356/446 |
| 4,527,898 | 7/1985 | Stapleton | 356/446 |
| 4,613,235 | 9/1986 | Suga | 356/446 |

OTHER PUBLICATIONS

Matsuta et al., "Development of Gloss Tester for Paint Coatings", Japanese Journal of Applied Physics, vol. 21, No. 1, Jan., 1982 pp. 133-136.

Primary Examiner—Edward P. Westin
Assistant Examiner—Charles F. Wieland
Attorney, Agent, or Firm—Warren D. Hill

[57] ABSTRACT

A single meter measures the gloss and the distinctness of image (DOI) of a painted surface for quality evaluation of the finish. A DOI signal is obtained by a prior method of focusing the reflected image of a moving shutter onto a slit and measuring the light passing through the slit. The rate of increase of the resulting signal is used as a measure of DOI. The same signal is integrated over a preset time period covering the upper part of the signal rise to yield a value proportional to gloss.

3 Claims, 3 Drawing Sheets

COMBINED DISTINCTNESS OF IMAGE AND GLOSS METER

FIELD OF THE INVENTION

This invention relates to an instrument for measuring the reflectivity of a surface and more particularly to such an instrument for measuring distinctness of image and gloss.

BACKGROUND OF THE INVENTION

To assess the quality of finished surfaces various schemes have been devised to measure some parameter and assign a figure of merit to the finish. For evaluating automotive paint or other finishes, two of the most important and generally accepted measurements are the distinctness of image and gloss. These are not used each to the exclusion of the other but rather they are employed together since they measure different surface characteristics. As a consequence, two separate meters are employed, each dedicated to a single parameter measurement. The extra cost and inconvenience of using two separate instruments is evident.

Surface reflectivity is a function of material properties such as index of refraction. Of the total light reflected some will be reflected at a specular angle and the remainder will be scattered at other angles. The specularly reflected portion is a measure of gloss. Thus rough surfaces and matte finishes tend to scatter the light and result in low gloss. Conventional gloss meters measure the light reflected through a small aperture at the specular angle and are calibrated to a standard index. The distinctness of image of a finish is a measure of the sharpness of images reflected from the surface. For example the edge of an image may be sharp or blurred to some degree. It depends on the scattering properties of the surface and the paint pigments and flakes. My previous patent, U.S. Pat. No. 4,527,898, disclosed a distinctness of image meter projecting a light onto a test surface and sensing the light reflected from the surface over a large angle and focused through an aperture. The light is interrupted by a moving blade near the source and the sharpness of the image at the aperture determines how rapidly the detected light level changes. The rate of change is a measure of the distinctness of image and depends on the amount of scattering while the maximum detected amplitude depends on the total reflected light. Thus all the information for determining the surface gloss is available in the detected light signal in the distinctness of image instrument. I have discovered that the gloss measurement can be made by my distinctness of image meter with a modification of the signal processing at substantially no additional cost.

SUMMARY OF THE INVENTION

It is therefore an object of the invention to provide a single instrument for measuring both distinctness of image and gloss of a surface finish.

The invention is carried out by a combined distinctness of image meter and gloss meter for measuring the reflective quality of a surface comprising: a light source and a light detector for respectively illuminating a surface being inspected and receiving light reflected from the surface, an aperture near one of the source and the detector, a motor driven chopper blade in the light path for interrupting the illumination and causing a reflection of the edge of the blade in the finish, means for focusing the reflected image of the blade onto the detector whereby the detector signal varies in accordance with reflective characteristics of the surface, and an electrical circuit for analyzing the rate of change of the detector signal to determine the distinctness of image of the surface and for integrating the area under a portion of the rising detector signal to obtain a measure of the surface gloss.

BRIEF DESCRIPTION OF THE DRAWINGS

The above and other advantages of the invention will become more apparent from the following description taken in conjunction with the accompanying drawings wherein like reference numerals refer to like parts and wherein:

Referring to FIG. 1 the meter 10 comprises a support 12 having feet 14 for resting on the panel 16 undergoing surface finish evaluation. A light source 18 including an LED 20, a collimating lens 22, and a diffuser 24 project a beam of light along an optical axis 25, represented as a broken line, onto the panel 16. A chopper 26 having a plurality of blades 28 is rotated by a motor 30 to periodically interrupt the light beam. The light beam is reflected from the panel and an image of each blade edge is focused by a lens 32 onto a slit or aperture 34 which is near a photodetector 36. The blades 28 are positioned at different distances from the center of the chopper so that for test panels of different curvatures one of the blades will be in substantial focus. A mirror 37 associated with one of the blades 28 intercepts the light beam once each revolution of the chopper 26 to send a light pulse to a photodetector 39 which generates a synch signal. Details of the instrument are presented in my patent U.S. Pat. No. 4,527,898 which is incorporated herein by reference.

FIG. 2 shows the image 28' of a chopper blade 28 as a shaded area as it is moving across the slit 34 in a direction to illuminate the slit. The detector output is a signal proportional to the light energy passing through the slit 34. If the reflected image 28' is sharp the detector output rises rapidly but if the image is blurry the rise rate is low. A measurement of the rise rate provides the distinctness of image value. The graph of detector output in FIG. 3 illustrates a typical signal. The rise rate is preferably measured by locating the amplitude midpoint M of the rising curve and and measuring the slope in that region.

When only the specularly reflected light is measured the gloss value can be directly obtained. In the subject meter the lens 32 subtends a large angle of the reflected light and thus captures scattered light in addition to the specular light and focuses it toward the detector 36. In FIG. 4, each part illustrates the incident beam 40, the surface 16a, 16b or 16c and the reflected beam 42a, 42b or 42c. The angular distribution of the reflected beam is shown graphically as a lobe having maximum amplitude on the axis of the reflected beam. The shaded portion of each lobe represents the specular light which would pass an aperture representing some standard small angle A of a gloss meter and the remainder or unshaded portions of the lobe represent the scattered light. The amount of light is represented by the area of the lobe or any given lobe portion. Due to the lens 32 the distinctness of image meter detects both types of reflected light. In FIG. 4, part a, the surface 16a has high reflectivity and a low degree of scattering. Thus the total lobe area is large and the unshaded portion is relatively small. In part b the surface 16b has a lower reflectivity as well as low scattering. Thus the lobe area is smaller than for surface 16a and the unshaded portion is correspondingly smaller. In part c the surface 16c has high reflectivity equal to that of surface 16a, resulting in a lobe area equal to that of part a, and a high degree of scattering resulting in a large unshaded portion.

Figure 5:
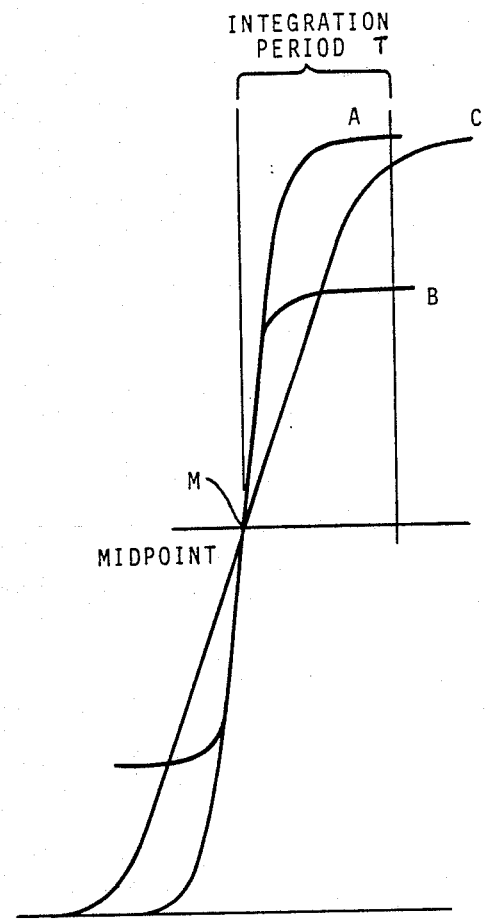
FIG. 5 is a graph illustrating detected light waveforms corresponding to the diagrams of FIG. 4.

As the surfaces 16a, 16b and 16c are evaluated by the meter 10, The corresponding detector outputs are shown in FIG. 5 as curves A, B and C respectfully. The curves are shown superimposed with coincident midpoints M. The curve amplitudes reveal the reflectivity of the surfaces, so that curves A and C reveal equal reflectivity as stated above. Curves A and B have the same rate of rise at the midpoints and thus have the same distinctness of image as measured by the meter 10.

Figure 3:
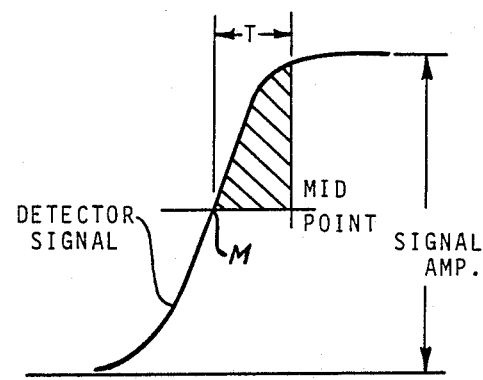
FIG. 3 is a graph of the detected light waveform of the meter.
Figure 4A:
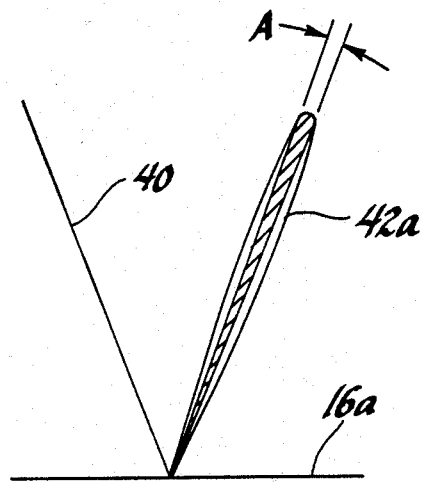
FIG. 4, a, b, and c are diagrams of reflected light intensity from different surfaces.
Figure 4B:
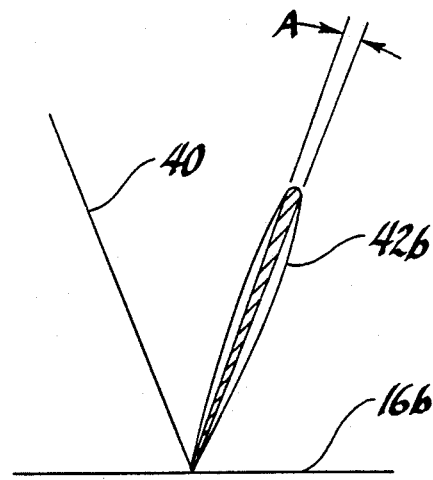
Figure 4C:
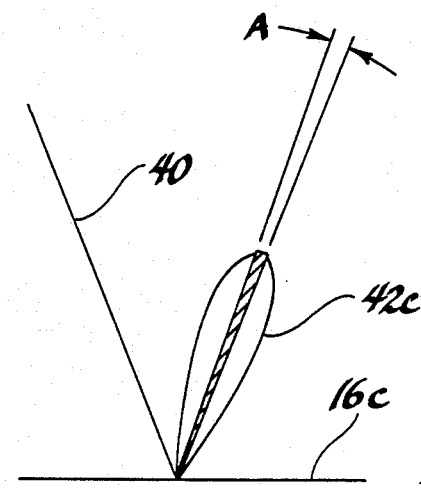

The gloss is a measure of the specular light (shaded lobe area) and that is a function of the total detected light (total lobe area) minus the scattered light (unshaded area). This gloss value is approximated by integrating the upper portion of the detector output signal over an empirically determined period T starting at the midpoint M. The integrated area is shown as the shaded area G in FIG. 3. For a given reflectivity the amount of scattering directly affects the integrated area: this is apparent from an inspection of the curves A and C of FIG. 5. The high level of scattering at surface 16c reduces the slope of the curve C and hence reduces the integrated area. On the other hand a comparison of the areas under curves A and B shows the effect of reduced reflectivity even though the proportion of scattered light and the distinctness of image remain the same.

Figure 6:
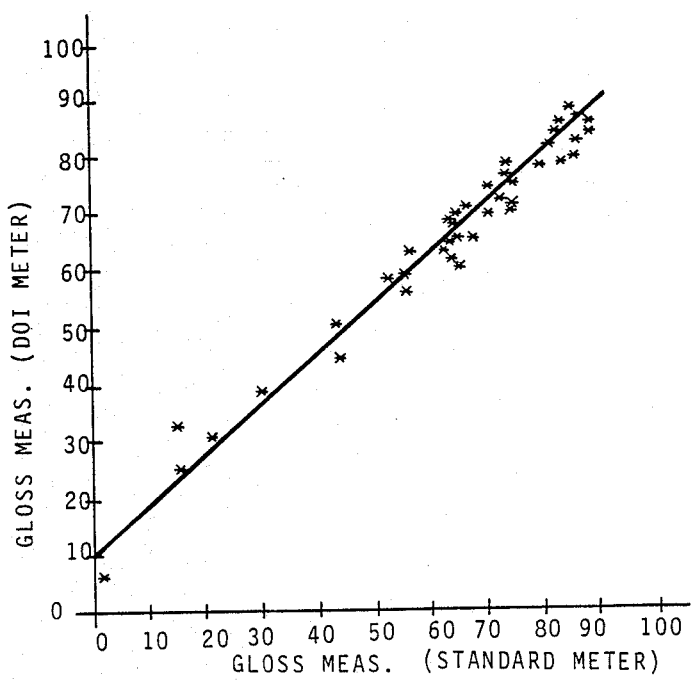
FIG. 6 is a chart of test results comparing the gloss readings of the subject meter to a conventional independent gloss meter.

The integration period T required to obtain results equivalent to conventional gloss meters is determined empirically. That is, readings on various surfaces are measured with ordinary gloss meters and the meter 10 and the period T is adjusted to get a good match of readings. For a chopper wheel period of 770 msec a period T of 4.25 msec was found to give good correlation with a standard gloss meter, provided a correction constant K is included. A formula of Gloss=k×G+K describes the relationship where k is a calibration factor. FIG. 6 shows the results of tests on many samples plotted to illustrate the substantially straight line relationship between the readings of meter 10 (DOI Meter) and a standard gloss meter. The offset K=−10 is evident from the y-intercept of the line and the slope or calibration factor k is also evident. In practice the meter is periodically calibrated against a standard panel to set the calibration constant k.

Figure 1:
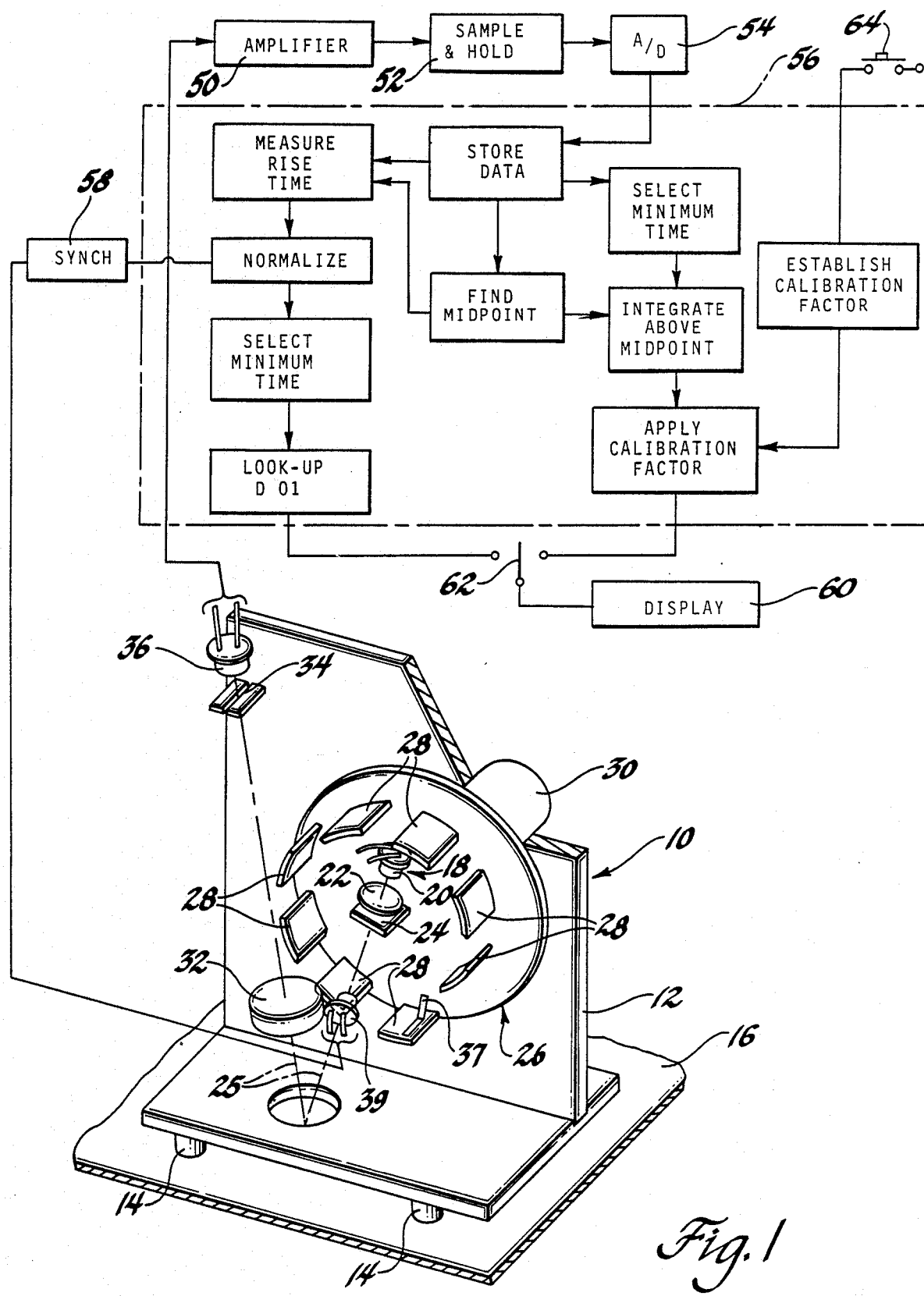
FIG. 1 is an isometric view and circuit diagram of a combined distinctness of image and gloss meter according to the invention.
Figure 2:
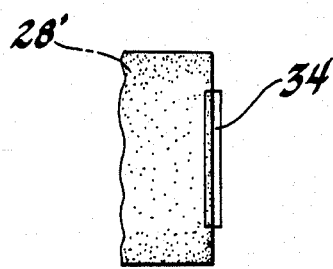
FIG. 2 is an illustration of the detector slit and the image of a chopper blade of the meter of FIG. 1.

The circuit for carrying out the gloss and distinctness of image measurements is shown in FIG. 1. An amplifier 50 coupled to the detector 36 output provides a signal to a sample and hold circuit 52 which stores several signal values during each signal rise, an analog-to-digital circuit 54 which digitizes the sampled values and passes them to the memory of a microcomputer 56 which is programmed to determine from the collected data the distinctness of image and gloss of the surface 16. The data is stored and the midpoint of each rise time is determined. The rise time is measured at the midpoint of each rise and the rise time is normalized for each blade by the synchronization circuit 58 which provides information on which chopper blade 28 is in the light path. Then, on the basis of the minimum rise time (highest rise rate), the distinctness of image is found in a lookup table. The microcomputer 56 drives a display 60 through a manually operated switch 62. Gloss is determined from the stored data by selecting the minimum rise time, integrating the rise time above the midpoint and applying the calibration factor to drive the display 60 through the switch 62. The calibration factor is established by operating the meter on a test panel of known gloss and manually closing a calibration switch 64 to enable a calibration function which selects the calibration factor k necessary to conform the displayed value to the known standard.

It will be seen that according to this invention gloss and distinctness of image can be measured by the same instrument and that the previous distinctness of image meter known from U.S. Pat. No. 4,527,898 is easily converted to include the new function by merely reprogramming the microcomputer and adding switch hardware. Various departures from the described meter may be made within the spirit of the invention. For example, the midpoint of the rising signal is the most convenient point to begin integration in the preferred embodiment but other points may be used for this purpose.

The embodiments of the invention in which an exclusive property or privilege is claimed are defined as follows:

1. A combined distinctness of image meter and gloss meter for measuring the reflective quality of a surface comprising:
   a light source and a light detector for respectively illuminating a surface being inspected and receiving light reflected from the surface,
   an aperture near one of the source and the detector,
   a motor driven chopper blade in the light path for interrupting the illumination and causing a reflection of the edge of the blade in the finish,
   means for focusing the reflected image of the blade onto the detector whereby the detector signal varies as a function of the total light and the scattered light received by the detector, and
   an electrical circuit responsive to the detector signal for determining the difference of the total light and the scattered light received by the detector to achieve a gloss measurement and for determining the distinctness of image.

2. A combined distinctness of image meter and gloss meter for measuring the reflective quality of a surface comprising:
   a light source and a light detector for respectively illuminating a surface being inspected and receiving light reflected from the surface,
   an aperture near one of the source and the detector,
   a motor driven chopper blade in the light path for interrupting the illumination and causing a reflection of the edge of the blade in the finish,
   means for focusing the reflected image of the blade onto the detector whereby the detector signal varies in accordance with reflective characteristics of the surface, and an electrical circuit for analyzing the rate of change of the detector signal to determine the distinctness of image of the surface and for integrating the area under a portion of the rising detector signal to obtain a measure of the surface gloss.

3. A combined distinctness of image meter and gloss meter for measuring the reflective quality of a surface comprising:

a light source and a light detector for respectively illuminating a surface being inspected and receiving light reflected form the surface, an aperture near the detector, a motor driven chopper blade in the light path for interrupting the illumination and causing a reflection of the blade edge in the finish, means for focusing the reflected image of the blade through the aperture onto the detector whereby the detector signal varies in accordance with reflective characteristics of the surface, and an electrical circuit for analyzing the rate of change of the detector signal to determine the distinctness of image of the surface and for integrating the area under an upper portion of the rising detector signal starting from the midpoint of the signal amplitude and extending over an empirically determined time to obtain a measure of the surface gloss.

* * * * *